United States Patent [19]

Pinchuk et al.

[11] Patent Number: 4,872,455
[45] Date of Patent: Oct. 10, 1989

[54] ANASTOMOSIS TRIMMING DEVICE AND METHOD OF USING THE SAME

[75] Inventors: Leonard Pinchuk; John B. Martin Jr., both of Miami, Fla.

[73] Assignee: Corvita Corporation, Miama, Fla.

[21] Appl. No.: 292,643

[22] Filed: Dec. 30, 1988

Related U.S. Application Data

[63] Continuation of Ser. No. 125,810, Nov. 25, 1987, abandoned, which is a continuation of Ser. No. 869,299, Jun. 2, 1986, abandoned.

[51] Int. Cl.$^4$ .............................................. A61B 17/32
[52] U.S. Cl. ...................................... 128/305; 30/92; 30/355
[58] Field of Search ............... 128/305, 751, 753, 754, 128/318; 30/92, 94, 112, 229, 230, 95, 355, 356, 1.5, 90.1, 320

[56] References Cited

U.S. PATENT DOCUMENTS

| | | | |
|---|---|---|---|
| 2,994,321 | 8/1961 | Tischler | 128/318 X |
| 3,701,352 | 10/1972 | Bosworth | 128/305 |
| 3,807,046 | 4/1974 | Igyarto et al. | 30/92 |
| 3,816,919 | 6/1974 | Portnoy | 128/305 |
| 4,597,385 | 7/1986 | Watson | 128/318 X |

Primary Examiner—Michael H. Thaler
Attorney, Agent, or Firm—Lockwood, Alex, Fitzgibbon & Cummings

[57] ABSTRACT

The anastomosis trimming device is used for trimming one end section of a tubular structure, such as a blood vessel or vascular graft, which is to be anastomosed, to provide the anastomotic end with a smooth, reproducible shape. The end is trimmed in such a manner as to mate with a similarly trimmed end of a second tubular structure or with an incision in the side of a second tubular structure. The device comprises first and second arms pivotably connected to each other at one end, with the first arm mounting a cutting die including a cutting element on a free end thereof. The cutting element faces toward the second arm, and the free end of the second arm mounts a mating element facing toward the first arm which, upon pivoting of the free ends of the first and second arm, mates with the cutting element on the first arm.

25 Claims, 3 Drawing Sheets

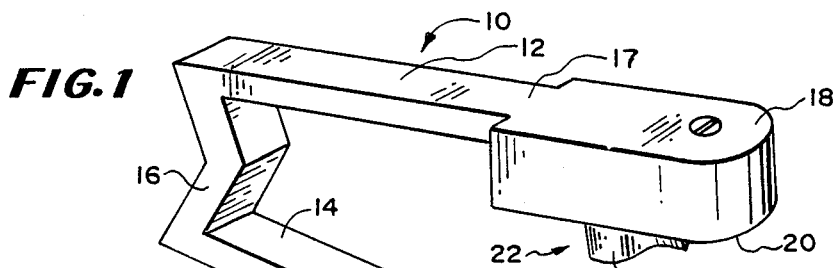
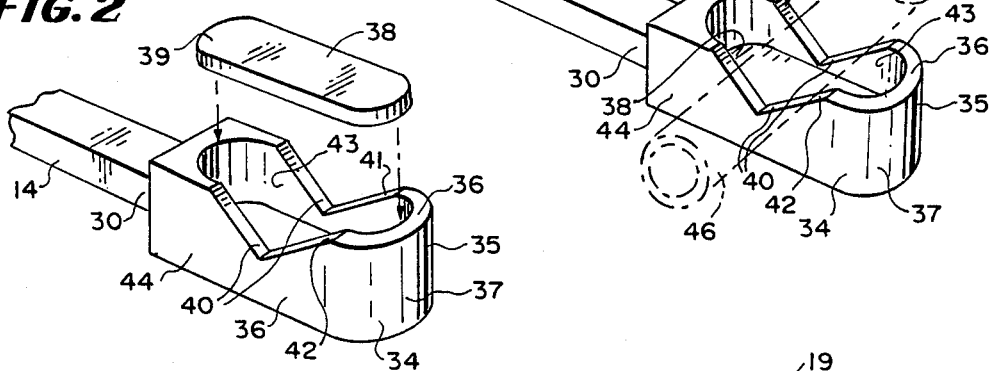
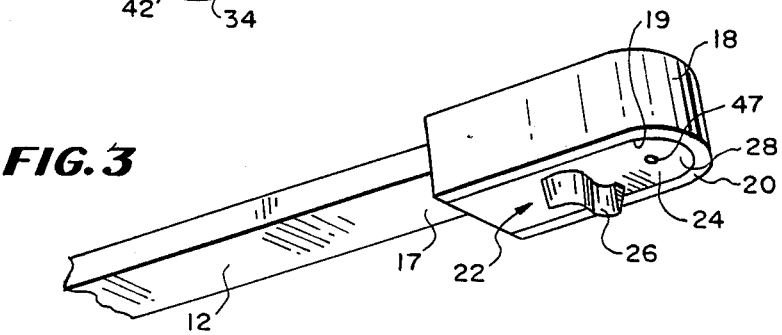
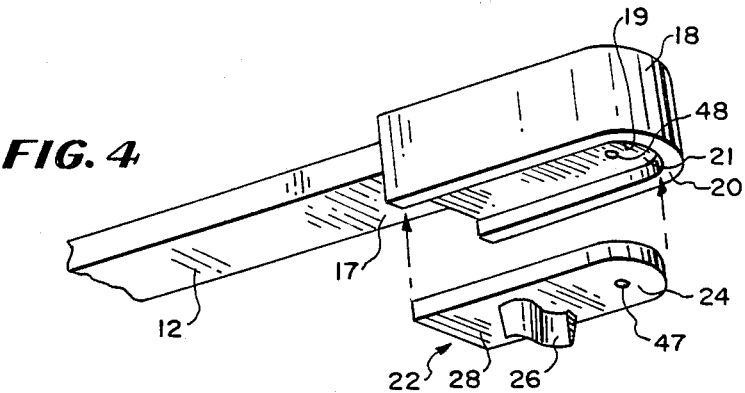

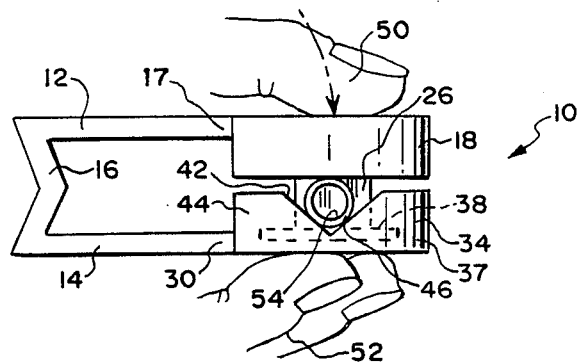
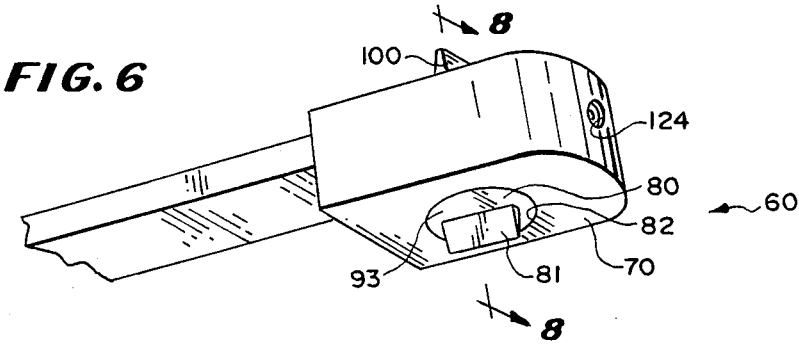
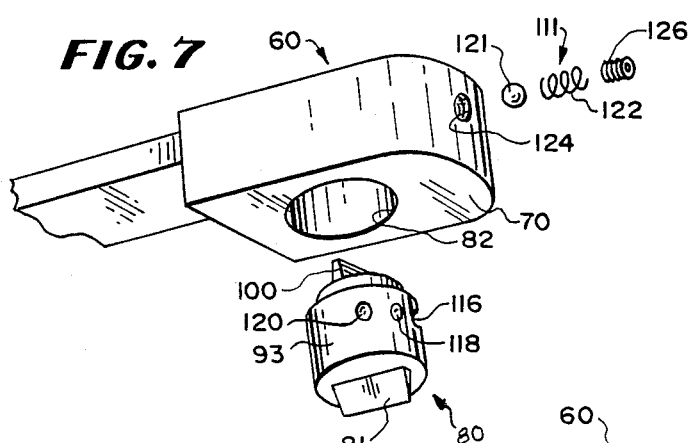
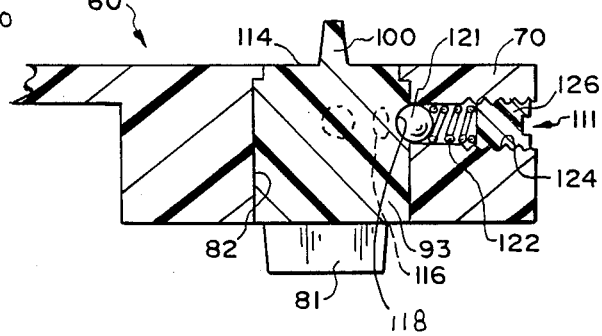
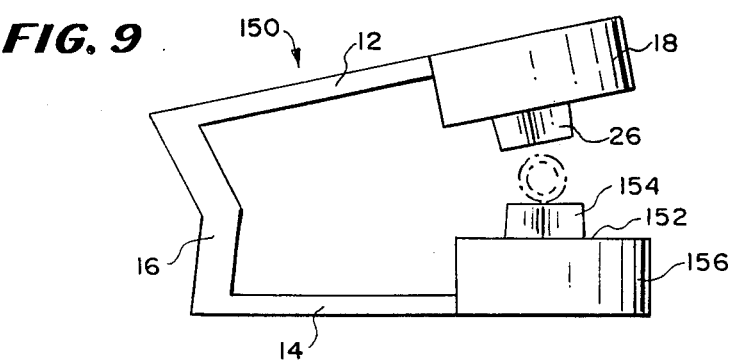

ANASTOMOSIS TRIMMING DEVICE AND METHOD OF USING THE SAME

This is a continuation of application Ser. No. 07/125,810, filed Nov. 25, 1987, abandoned, which is a continuation of application Ser. No. 869,299, filed June 2, 1986, abandoned.

BACKGROUND OF THE INVENTION

1. Field of the Invention

The present invention relates to a device for preparing an end of a tubular structure, such as a blood vessel, which is to be anastomosed, and more particularly to an anastomosis trimming device.

2. Description of the Prior Art

Heretofore in the field of cardiovascular surgery, when it has been necessary to perform an anastomosis, i.e., to suture two blood vessels together while assuring that the lumen remains open, the shaping of the anastomotic end of the vessels has usually been achieved by the use of scissors.

With respect to forming an anastomosis, it is to be noted that one of the vessels is usually the patient's blood vessel and the other vessel may be a blood vessel or tissue graft from the same patient, a synthetic graft, a biograft, a homograft, a heterograft, a renograft, or a biosynthetic graft.

Further, it is to be noted that for preparing the end surfaces which are to be joined together in an anastomosis procedure, particular matched geometries are required for the ends of the vessels to be anastomosed end-to-end for reduction of potential weakness or leakage in the area of the anastomosis. By geometry, one means various shapes of cuts applied to the anastomotic ends, the geometry generally being dictated by the type of anastomosis to be performed, and by the location in the body where the anastomosis is to be formed.

Difficulties have presented themselves when the ends of graft structures are manually trimmed with scissors, inasmuch as such scissor trimming technique lacks exact reproducibility and therefore provides a variability between opposed ends, i.e. inexact mating within the anastomotic site, such inexact mating causing a potential site of leakage.

Various geometries of cut, i.e. straight cut, sigmoid cut, spatulate cut, and the ratio of the lumen's longitudinal diameter to the diameter of the graft, all dictate the necessity of the provision of a device which will allow for reproducibility when trimming ends of vessels and/or synthetic graft structures which are to be joined. In this respect, unless the vessel is cut with one continuous stroke, nicks and irregularities can result. Such irregularities can produce a site of tearing or leakage when high internal pressures are applied, or after a prolonged period of use. When trimming a vessel in-situ, and most significantly when a sigmoid shape is required, maneuvering scissors in such a restricted area will provide difficulties in achieving a smooth end surface, especially if the vessel to be cut is thickwalled.

It is therefore desirable that the anastomosis trimming device of the present invention provide a compact, easily manipulated means for cutting or trimming the ends of blood vessels or grafts with the shape of the end cut or trim being reproducible onto each anastomotic end of the structures that are to be connected end-to-end in an anastomotic manner.

Further, the anastomosis trimming device can be utilized in providing a smooth cut end for use in bypass procedures, where end-to-side anastomoses are required. The anastomosis trimming device can also be used for trimming other tubes or conduits such as ureters, urethras and the like.

In particular, the anastomosis trimming device of the present invention provides a cutting die incorporating a cutting element and, preferably, an opposed, mating element, such as a seat member, anvil, or cutting element, specifically providing for uniformity of cuts at the ends of the structures to be anastomosed, with the geometry of the cutting element of the cutting die utilized dictating the reproducible shape of the anastomotic ends. The anastomisis trimming device can be made inexpensively from one molded piece and can be discarded or it can be resterilized for multiple uses.

SUMMARY OF THE INVENTION

According to the invention there is provided a reuseable/disposable device for trimming an end section of a tubular structure, such as a vascular graft or a blood vessel which is to be sutured to another tubular structure, to provide the trimmed end with a smooth, reproducible shape, the end being trimmed in such a manner as to mate with the second tubular structure, to form an end-to-end anastomosis, or to mate with an incision on the side of a structure to form an end-to-side anastomosis, said device comprising: first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier; said cutting blade having a curvalinear shape along the length thereof and said cutting blade extending a predetermined distance outwardly from said carrier, which distance is equal along the length of the blade, and facing toward said opposing surface of said second element mounting structures; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive and end section of a tubular structure therein, said tubular structure extending across said mating element and being maintained in alignment relative to said cutting element by said alignment means to provide means by which an end section of said tubular structure can be reproducibly trimmed.

BRIEF DESCRIPTION OF THE DRAWINGS

FIG. 1 is a perspective view of one embodiment of the anastomosis trimming device of the present invention.

FIG. 2 is a fragmentary perspective view of one embodiment of a mating element of the anastomosis trimming device.

FIG. 3 is a fragmentary perspective view of one embodiment of a cutting die positioned within a die carrier of the anastomosis trimming device.

FIG. 4 is a fragmentary perspective view of the cutting die and die carrier of the anastomosis trimming device.

FIG. 5 is a side view of the anastomosis trimming device of the present invention and shows the device as used for trimming an anastomotic end of a vessel or graft.

FIG. 6 is a fragmentary perspective view of yet another embodiment of the cutting die and die carrier of the anastomosis trimming device of the present invention.

FIG. 7 is an exploded perspective view of the cutting die shown in FIG. 6.

FIG. 8 is a sectional view through the cutting die shown in FIG. 6 and is taken along line 8—8 of FIG. 6.

FIG. 9 is a side view of a further embodiment of the anastomosis trimming device of the present invention.

DESCRIPTION OF THE PREFERRED EMBODIMENT

Figure 10:
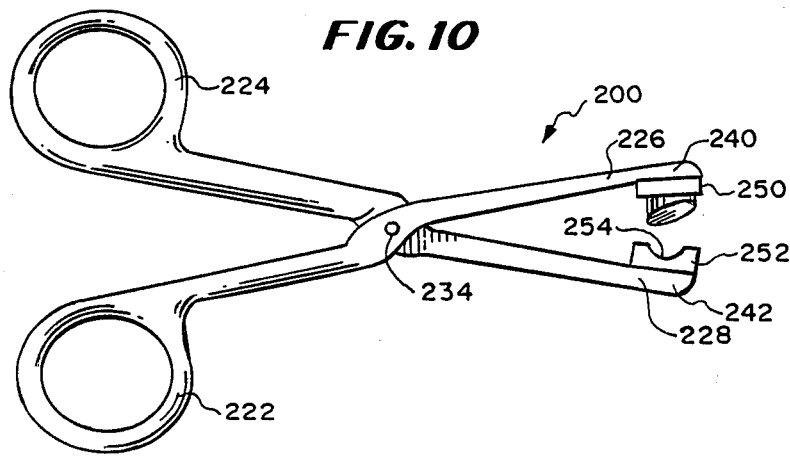
FIG. 10 is a side view of yet another embodiment of the anastomosis trimming device of the present invention.

Referring now to the drawings in greater detail, there is illustrated in FIG. 1 one embodiment of an anastomosis trimming device 10 constructed according to the teachings of the present invention. The trimming device 10 has two arms 12 and 14 joined at one end by a hinge portion 16. Preferably, the arms 12 and 14 and hinge portion 16 are made of a single injection molded piece of polycarbonate or other similar material with the device 10 having a staple-puller-like configuration.

In this embodiment, a free end 17 of the arm 12 is provided with an integral die carrier 18. The die carrier 18 is elongate, having an elongate axis generally in line with the elongate axis of the arm 12. This die carrier 18 comprises a hollow horseshoe-shaped cup formation 19 (FIG. 4). A rim 20 of the cup formation 19 faces toward the opposing arm 14 and the cup formation 19 has a hollow 21 (FIG. 4) which is defined by the rim 20. A cutting die assembly 22 is inserted into the hollow 21 and comprises a plastic blade carrier or base portion 24 which is configured to be snugly received within the hollow 21 of the cup formation 19 and a stainless steel sigmoid cutting element 26. The base portion 24 is dimensioned in such a manner as to be flush along the rim 20 of the cup formation 19 when positioned within the hollow 21 and has, at approximately the center thereof and on an outwardly facing side 28 thereof, the sigmoid cutting element 26 which extends a predetermined distance outwardly from the base portion 24 toward the opposing arm 14. It is understood that base portion 24 is held in hollow 21 with the aid of a screw (not shown) that is located through the die carrier 18 and is threaded into the blade carrier or base portion 24.

A free end 30 of the opposing arm 14 has mounted thereon a mating element 34 comprising, in this embodiment, a cutting block 35 which is also elongate and has an elongate axis generally in line with the long axis of the arm 14. A rim 36 of mating element 34, when the arms 12 and 14 are brought together, matingly engages against rim 20 of the cup formation 19 in a press fit relationship (FIG. 5). The mating element 34, in this embodiment, comprises a housing 37, having at the center thereof, a recessed seat member 38 having a cutting board-like surface 33. The seat member 38 is preferably made of a polymer material which is softer than polycarbonate but which has a Shore hardness greater than 60A, such as a material taken from the group consisting of polyurethane, polypropylene, acrylic butadiene styrene (ABS) or the like.

When the arms 12 and 14 are flexed toward each other, the cutting board-like surface 39 of the seat member 38, by reason of its recessed position within the housing 37, bears directly against the cutting element 26 of the cutting die 22.

Turning now to FIG. 2, it will be understood that the seat member 38 may be formed in such a manner as to be separable from the housing 37 so that it can be replaced when necessary, such as when it becomes worn or for cleaning after many cuttings.

As shown in FIGS. 1 and 2, the housing 37 can also be provided with an alignment or guide formation 40, which in this embodiment is defined by V-shaped notches 41,42 which are cut into opposed sidewalls 43,44 of the housing 37 As illustrated in phantom in FIG. 1, a blood vessel 46 can be positioned across the housing 37 and within the notches 41,42 to align the vessel 46 relative to the cutting element 26.

As shown in FIGS. 3 and 4, the base portion 24 of the cutting die 22 has the shape of a rectangle with a radiused end, e.g., a tombstone shape, and is positioned within the U-shape hollow 21 of the cup formation 19 of the die carrier 18. The cutting die 22 can be replaced with another cutting die 22 having a different shaped cutting element 26 to allow for different shaped trims or cuts to be applied to an anastomotic end of a tubing, i.e. vessel 46, as will be described in greater detail hereinafter. It is to be noted that the cutting die 22 can be slid into the U-shaped hollow 21 through the open end of the U and can be screwed into place or held securely in place by means of a ball and notch configuration, a force fit or the like. Holes 47, in base portion 24, and 48 in die carrier 18 can be provided for this purpose, i.e., for receiving a screw (not shown).

Referring now to FIG. 5, in the use of the anastomosis trimming device 10, a user places the trimming device 10 between thumb 50 and one or two fingers 52. An end 54 of the vessel 46 which is to be anastomosed is placed within the notches 41,42. Once the tubular structure 46 is seated in the notches 41,42 of the housing 37, one merely flexes the arms 12 and 14 toward each other by use of the thumb 50 and two fingers 52 as shown, and a precise trim or cut (FIGS. 11-13) is produced on the end 54 of the vessel 46 by the cutting element 26.

With such precise alignment of the vessel 46 relative to the cutting element 26, numerous cuts can be made with the device 10 using the cutting element 26 and such cuts will be substantially identical to each other. Such reproducibility is desirable when forming an end-to-end anastomosis insofar as inexact mating ends, i.e., ends which have been cut by scissors or the like and have a cut shape which has not been perfectly reproduced on each end to be anastomosed, can provide a weak area or an improper seating of an anastomosis which, under high pressure, or after a period of extended use, can become prone to leakage or blood clots (if the lumens are not aligned).

Also, the end 54 can be mated with an incision in the side of another vessel for forming an end-to-side anastomosis.

Referring now to FIG. 6, there is disclosed therein another embodiment of an anastomosis trimming device 60 comprising a die carrier 70 and a cutting die 80 including a cutting element 81 which provides a straight cut to an end of a vessel 46 to be anastomosed. The die carrier 70 in this embodiment 60 is provided with a vertically disposed central throughbore 82 within which the cutting die 80 is rotatably mounted.

Figure 11:
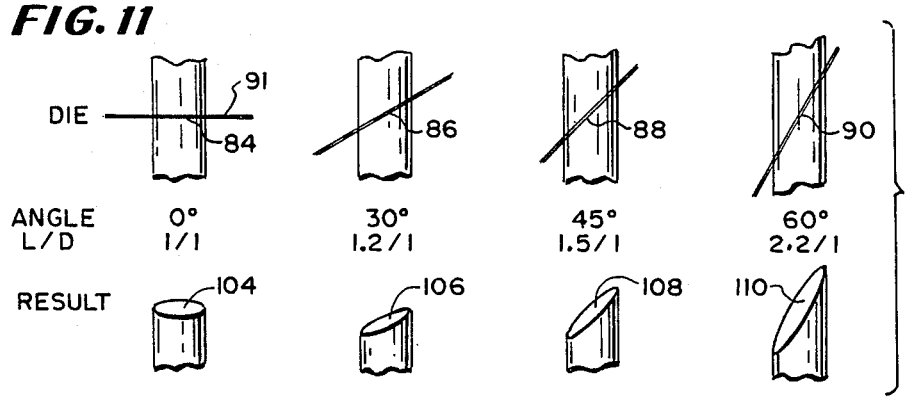
FIG. 11 is a set of four views of angles of cut which can be obtained by use of the anastomosis trimming device of the present invention when a straight cut die is inserted into the die carrier of the device for four length-to-diameter ratios of cuts and of four views of the resultant cut end shapes of vessels which have been trimmed with this anastomosis trimming device constructed according to the teachings of the present invention.

Various straight lines of cut 84, 86, 88, 90 (FIG. 11) at different angles, relative to a line 91 normal to the elongate axis of the vessel 46, which can be made with the device 60 are shown in FIG. 11. Typical angles for straight lines of cut are 0 degrees, 30 degrees, 45 degrees or 60 degrees, to the line 91.

Referring now to FIGS. 7 and 8, a base portion 93 of the cutting die 80 is cylindrical and is received within the throughbore 82 of the die carrier 70. Such cylindrical base 93 may be provided with a tab 100 or like mechanism to allow a user of the anastomosis trimming device 60 to rotate and index with two fingers, the cutting die 80 within the throughbore 82 to any position required to provide a straight line of cut 84, 86, 88, 90, having a desired angle.

A spring loaded releasable locking mechanism 111 is provided in the die carrier 70 for engaging and releasably holding the cutting die 80 at respective positions which will provide the straight line of cut 84, 86, 88, 90 having the different desired angles. The cut tubing ends are shown in FIG. 11 and identified with reference numerals 104, 106, 108 and 110. For this purpose, the cutting die 80 has four pockets 114, 116, 118 (FIG. 8) and 120 (FIG. 7) on the cylindrical surface of the base 93.

The mechanism 111 includes a ball 121 biased by a spring 122 which are received in a bore 124 in the die carrier 70. The ball 121 and spring 122 are held in the bore 124 by a set screw 126 and the ball 121 is biased toward the base 93 and when received in a pocket, e.g. pocket 118 (FIG. 8), releasably locks the cylindrical base 93 against rotation to set the cutting element at a desired angle.

When a user has chosen a particular angle of cut, he merely turns the cutting die 80 by means of the tab 100 until the desired relative angular position of the cutting element 81 is obtained, at which point the ball 121 of the releasable locking mechanism 111 is received within a specific pocket 114, 116, 118 or 120. Once the ball 121 is received within a specific pocket and releasably locks the die against rotation, any number of cuts can be made with the trimming device 60 and each cut will be substantially identical to the last cut. In other words, as long as the ball 121 is spring biased in that pocket, e.g. pocket 118 in FIG. 8, and each vessel 46 is aligned within alignment notches 41,42 provided in a housing 37 of a mating element 34, each cut ill be reproducible and will provide a smooth trimmed end to the tubing or vessel 46.

Turning now to FIG. 9, there is illustrated therein a further embodiment of an anastomosis trimming device 150 which is a modification of the device 10 shown in FIG. 5 and which is constructed in accordance with the teachings of the present invention. For identical parts, the same reference numerals are used in FIG. 9 as are used in FIG. 5.

In this embodiment, one merely replaces the cutting block 35 utilized as the mating member 34 with a second cutting die 152 including a cutting element 154 and a die carrier 156. The cutting element 154 is arranged to shear with cutting element 26 or 81 such that a scissor-like trimming or cutting of the end of the vessel 46 is obtained.

In another alternative embodiment illustrated in FIG. 10, an anastomosis trimming device 200 is a scissor-type device comprising two handle portions 222,224 extending to blade portions 226,228 with one handle portion 222 and blade portion 226 being joined to the other handle portion 224 and blade portion 228 at a pivot 234.

The blade portions 226,228 do not contact each other as in a conventional scissor arrangement. Rather the blade portion 226, 228 mount on their respective distal ends 240,242, a cutting element 250 and seat or cutting element 252 similar to that shown in FIG. 1 or similar to that shown in FIG. 9. The blade portions 226,228 are movable toward each other to bring cutting element 250 against seat or cutting element 252 for cutting a tubing or vessel received therebetween and seated in a notched guide formation 254.

The device 200 is very useful in deep artery anastomoses where the user's hand cannot be inserted into an area within a deep incision.

Any or all of the embodiments of the anastomosis trimming device 10, 60, 150 or 200 described above may be provided as a reuseable, sterilizable device or may be provided as a disposable device or as a combination of a sterilizable device with disposable blade assemblies and disposable seat members having the cutting board-like surface.

For example, the embodiment 60 defined in FIGS. 6-8 may be provided in a sterilizable form so that the user can, if desired, acquire several such devices 60, each having a particular cutting element 26.

Further, as an alternative, and with reference to the device 10 shown in FIG. 1, the body of the device 10 including the arms 12, 14 and hinge 16, can be reuseable, with the replaceable cutting die 22 and seat element 38 being either disposable or sterilizable.

As described above, various geometries of cut are required for various forms of anastomoses and bypass procedures typically performed.

Figure 12:
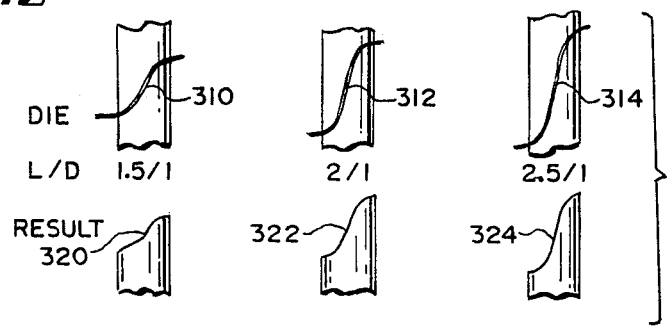
FIG. 12 is a set of three views of the angles of cut which can be obtained by use of the anastomosis trimming device of the present invention when a sigmoid cut die is inserted into the die carrier thereof, for three length-to-diameter ratios of cuts and of three views of the resultant cut end shapes of vessels which have been trimmed with this anastomosis trimming device constructed according to the teachings of the present invention.
Figure 13:
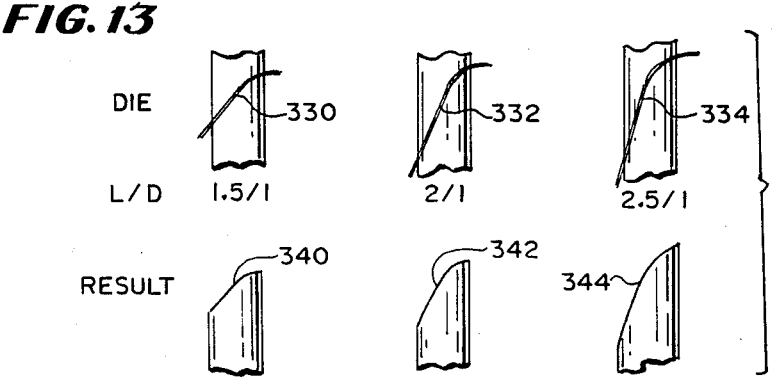
FIG. 13 is a set of three views of the angles of cut which can be obtained by use of the anastomosis trimming device of the present invention when a spatulate cut die is inserted into the die carrier thereof, for three views of length-to-diameter ratios of the cuts and of three views of the resultant cut end shapes of vessels which have been trimmed with this anastomosis trimming device constructed according to the teachings of the present invention.

Various primary geometries are shown FIGS. 11–13.

As described above, and with reference to FIG. 11, the cutting die 80 with straight line cutting element 81, can be positioned at varying angles to the line 91 of the tubular structure 46, to produce the resultant trimmed or cut ends 102, 106, 108 or 110 having varying luminal extents and angles of cut.

Further, the sigmoid cutting element 26 having various length-to-diameter ratios can provide cut or trimmed ends as shown in FIG. 12.

In FIG. 12, various length-to-diameter-ratio sigmoid cuts 310, 312 and 314 obtained with a sigmoid cutting element are shown. Further illustrated are the cut ends 320, 322 and 324 of a vessel so formed with the cuts 310, 312 or 314.

In FIG. 13, various length-to-diameter-ratio spatulate cuts 330, 332, and 334 obtained with a spatulate-shaped cutting element are shown and the cut ends 340, 342 or 344 so formed with the cuts 330, 332 or 334 are illustrated.

It will be apparent from FIGS. 11–13 that the greater the deviation of the cut from a line normal to the long axis of the tubing or vessel, the greater the luminal extent provided to the cut end of the tubing or vessel. Also, although various specific geometries of cut and variations thereof are set forth in the Figures, these are not to be construed as limiting. The specific geometries and variations thereof illustrated herein are only set forth as examples and other geometries of cut can be used.

The anastomosis trimming devices 10, 60, 150 and 200 have a number of advantages, some of which have been described above and others of which are inherent in the invention. Accordingly, the scope of the invention is only to be limited as necessitated by the accompanying claims.

We claim:

1. A reuseable/disposable device for trimming an end section of a tubular structure, such as a vascular graft or a blood vessel which is to be sutured to another tubular structure, to provide the trimmed end with a smooth, reproducible shape, the end being trimmed in such a manner as to mate with the second tubular structure, to form an end-to-end anastomosis, or to mate with an incision on the side of a structure to form an end-to-side anastomosis, said device comprising first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier; said cutting blade having a curvilinear shape along the length thereof and said cutting blade extending a predetermined distance outwardly from said carrier, which distance is equal along the length of the blade, and facing toward said opposing surface of said second element mounting structure; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive an end section of a tubular structure therein, said tubular structure adapted to extend across said mating element and be maintained in alignment relative to said cutting element by said alignment means to provide means by which an end section of said tubular structure can be reproducibly trimmed.

2. The device of claim 1 including a hinge formation connecting said element mounting structures together.

3. The device of claim 2 wherein said first and second element mounting structures and hinge therebetween are formed as a single integral structure.

4. The device of claim 1 wherein said first and second element mounting structures are pivotably connected together intermediate the ends thereof in a scissor arrangement.

5. The device of claim 1 being made of polycarbonate, acetyl resin, or the like.

6. The device of claim 1 wherein said means for mounting a replaceable cutting element includes a die carrier which has a U-shaped hollow and which receives a replaceable cutting element therein.

7. The device of claim 6 wherein said blade carrier of said cutting element is tombstone shaped and is slidable into said U-shaped die carrier at the open end of said U.

8. The device of claim 1 wherein said mounting means on said second element mounting structure comprise a housing.

9. The device of claim 8 wherein said housing is formed integral with said second element mounting 10. The device of claim 8 wherein said mating element comprises a seat member.

11. The device of claim 10 wherein said seat member is made of a polymer material soft enough not to dull the cutting blade but hard enough to support an item being cut.

12. The device of claim 10 wherein said seat member is removably mounted in said housing.

13. The device of claim 1 wherein said alignment means is defined by a pair of notches, each formed in an opposing wall of said housing, said notches being equidistantly spaced from an end edge of said housing.

14. The device of claim 1 wherein said first and second element mounting structures are of equal length.

15. The device of claim 1 wherein said mounting means on said first and second element mounting structures are approximately equal in dimension.

16. The device of claim 1 wherein said cutting element is rigidly fixed to said mounting means.

17. A reusable/disposable device for trimming an end section of a tubular structure, such as a vascular graft or a blood vessel which is to be sutured to another tubular structure, to provide the trimmed end with a smooth, reproducible shape, the end being trimmed in such a manner as to mate with the second tubular structure, to form an end-to-end anastomosis, or to mate with an incision on the side of a structure to form an end-to-side anastomosis, said device comprising: first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier and being rotatable within said mounting means; said cutting blade extending a predetermined distance outwardly from said carrier, which distance is equal along the length of the blade, and facing toward said opposing surface of said second element mounting structure; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive an end section of a tubular structure therein, said tubular structure adapt to extend said mating element and be maintained in alignment relative to said cutting element by said alignment means to provide means by which an end section of said tubular structure can be reproducibly trimmed.

18. The device of claim 17 wherein said cutting element has means for rotating said cutting element.

19. The device of claim 17 wherein said cutting element and mounting means include a releasable locking mechanism for releasably locking said cutting element in various rotated positions thereof.

20. The device of claim 19 wherein said releasable locking mechanism includes a bore in a wall of said housing, a ball and spring in said bore and pockets in an outer wall surface of said blade carrier, said blade carrier being rotatable to positions where one of said pockets is aligned with said ball such that said ball is spring biased into said pocket releasably to lock said cutting die against rotation.

21. The device of claim 20 wherein said mounting means has a cylindrical throughbore extending transverse to the long axis of said first element mounting structure and said blade carrier includes a cylindrical base which is received in said throughbore.

22. A reuseable/disposable device for trimming an end section of tubular structure, such as a vascular graft or a blood vessel which is to be sutured to another tubular structure, to provide the trimmed end with a smooth, reproducible shape, the end being trimmed in such a manner as to mate with the second tubular structure, to form an end-to-end anastomosis, or to mate with an incision on the side of a structure to form an end-to-side anastomosis, said device comprising: first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier; said cutting blade having along its length a portion which is straight and a portion which is curved and said cutting blade extending a predetermined distance outwardly from said carrier, which distance is equal along the length of the blade, and facing toward said opposing surface of said second element mounting structure; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive an end section of a tubular structure therein, said tubular structure adapted to extend across said mating element and be maintained in alignment relative to said cutting element by said alignment means to provide means by which an end section of said tubular structure can be reproducibly trimmed.

23. A reuseable/disposable device for trimming an end section of a tubular structure, such s a vascular graft or a blood vessel which is to be sutured to another tubular structure, to provide the trimmed end with a smooth, reproducible shape, the end being trimmed in such a manner as to mate with the second tubular structure, to form an end-to-end anastomosis, or to mate with an incision on the side of a structure to form an end-to-side anastomosis, said device comprising: first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier; said cutting blade having a sigmoid shape along the length thereof and said cutting blade extending a predetermined distance outwardly from said carrier, which distance is equal along the length of the blade, and facing toward said opposing surface of said second element mounting structure; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive an end section of a tubular structure therein, said tubular structure adapted to extend across said mating element and be maintained in alignment relative to said cutting element by said alignment means to provide means by which an end section of said tubular structure can be reproducibly trimmed.

24. A reusable/disposable device for trimming an end section of a tubular structure, such as a vascular graft or a blood vessel which is to be sutured to another tubular structure, to provide the trimmed end with a smooth, reproducible shape, the end being trimmed in such a manner as to mate with the second tubular structure, to form an end-to-end anastomosis, or to mate with an incision on the side of a structure to form ana end-to-side anastomosis, said device comprising; first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier; said cutting blade having along its length a first curved portion and a second curved portion and said cutting blade extending a predetermined distance outwardly from said carrier, which distance is equal along the length of the blade, and facing toward said opposing surface of said second element mounting structure; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive an end section of a tubular structure therein, said tubular structure adapted to extend across said mating element and be maintained in alignment relative to said cutting element by said alignment means to provide means by which an end section of said tubular structure can be reproducibly trimmed.

25. A method for trimming an end of a tubular structure, such as a blood vessel, urethra or the like, which is to be sutured to another identically trimmed tubular structure to provide the trimmed end with a smooth, reproducible shape, the end being cut in such manner as to mate with the trimmed end of the second tubular structure, to form an end-to-end anastomosis, or to mate with an incision on the side of a structure to form an end-to-side anastomosis using a device comprising: first and second element mounting structures coupled to each other in a manner allowing at least one of said structures to move relative to the other structure and each having an elongate axis and an opposing surface; said opposing surface of said first element mounting structure including means for mounting a replaceable cutting element parallel to said elongate axis thereof; said cutting element including a blade carrier and a single-edged, cutting blade of predetermined length mounted approximately centrally of said carrier; said cutting blade having a curvilinear shape along the length thereof and said cutting blade extending a predetermined distance outwardly from said carrier, which distance is equal along the length of the blade, and facing toward said opposing surface of said second element mounting structure; said opposing surface of said second element mounting structure including means for mounting a replaceable mating element parallel to said elongate axis thereof; said mating element having a cutting board-like surface which faces said cutting element and which, upon movement of one of said first and second element mounting structures toward the other structure, bears against said blade of said cutting element along the length of said blade; said mounting structure for said mating element including alignment means adapted to receive an end section of a tubular structure therein, said tubular structure adapted to extend across said mating element and be maintained in alignment relative to said cutting element by said alignment means to provide means by which an end section of said tubular structure can be reproducibly trimmed said method comprising:

choosing a desired cutting element;

inserting the desired cutting element into said mounting means of the first element mounting structure of the device;

positioning the cutting element in said mounting means to a desired cutting position for the anastomosis to be formed;

securing the cutting element in the desired position;

placing an end portion of a tubular structure across the opposing surface of the mating element;

aligning the tubular structure relative to the cutting element;

maintaining the aligned position; and causing relative movement between the cutting element and the mating element toward one another until they fit against one another and cut the end of the tubular structure to have a desired shape.

* * * * *

UNITED STATES PATENT AND TRADEMARK OFFICE
CERTIFICATE OF CORRECTION

PATENT NO. : 4,872,455

DATED : October 10, 1989

INVENTOR(S) : Leonard Pinchuk and John B. Martin, Jr.

It is certified that error appears in the above-identified patent and that said Letters Patent is hereby corrected as shown below:

```
    Col. 2, line 39, "curvalinear" should read --curvilinear--.
    Col. 6, line 14, "ill" should read --will--.
    Col. 9, line 18, "adapt" should read --adapted--.
    Col. 10, line 16, "such s a vascular" should read
--such as a vascular--; line 62, "ana" should read --an--.
```

Signed and Sealed this

Twenty-third Day of April, 1991

Attest:

HARRY F. MANBECK, JR.

Attesting Officer

Commissioner of Patents and Trademarks